United States Patent [19]

McAlpine et al.

[11] Patent Number: 5,171,740
[45] Date of Patent: Dec. 15, 1992

[54] COUMAMIDINE COMPOUNDS

[75] Inventors: James B. McAlpine, Libertyville, Ill.; Robert J. Theriault, Kenosha, Wis.; James P. Karwowski, Mundelein, Ill.; Marianna Jackson, Waukegan, Ill.; Randal H. Chen, Buffalo Grove, Ill.

[73] Assignee: Abbott Laboratories, Abbott Park, Ill.

[21] Appl. No.: 743,311

[22] PCT Filed: Oct. 10, 1989

[86] PCT No.: PCT/US89/04556
§ 371 Date: May 28, 1991
§ 102(e) Date: May 28, 1991

Related U.S. Application Data

[63] Continuation-in-part of Ser. No. 260,853, Oct. 21, 1988.

[51] Int. Cl.[5] .................... A61K 31/73; A61K 35/00; C07H 15/20; C12P 19/12; C12P 1/06; C12N 1/22; C12R 1/01

[52] U.S. Cl. ..................................... 514/53; 424/118; 435/100; 435/169; 435/252.1; 435/822; 536/13.1

[58] Field of Search .................... 435/100, 169, 252.1, 435/822; 536/13.1; 424/118; 514/53

[56] References Cited

U.S. PATENT DOCUMENTS

| 4,351,769 | 9/1982 | Whaley et al. ................. 260/326.34 |
| 4,482,707 | 11/1984 | Sakakibara et al. ............... 536/16.8 |
| 4,515,942 | 5/1985 | Iwasaki et al. ..................... 536/16.8 |
| 5,081,023 | 1/1992 | Yaginuma et al. .................... 435/76 |

OTHER PUBLICATIONS

Jackson et al., (1989) *J. Antibiot.*, 42(4), 527–532.
Chem. et al., (1989) *J. Antibiot.*, 42(4), 533–537.
Fernandes et al., (1989) *J. Antibiot.*, 42(4), 538–541.

*Primary Examiner*—Douglas W. Robinson
*Assistant Examiner*—Jon P. Weber
*Attorney, Agent, or Firm*—Andreas M. Danckers

[57] ABSTRACT

A mixture of new coumamidine compounds are produced by a microorganism, belonging to the genus *Saccharopolyspora*. The compounds have antibiotic activity against a broad spectrum of bacteria.

5 Claims, 4 Drawing Sheets

FIG. 1 H NMR SPECTRUM (500 MHz) IN D₂O OF COUMANIDINE gamma 1

FIG. 2  H NMR SPECTRUM (500MHz) IN $D_2O$ OF COUMANIDINE gamma 2

COUMAMIDINE COMPOUNDS

This is a continuation in part of U.S. patent application Ser. No. 260,853, filed Oct. 21, 1988.

TECHNICAL FIELD

This invention relates to a mixture of compounds, two new coumamidine compounds and a process for making them.

BACKGROUND OF THE INVENTION

The compounds of the present invention are similar to the family of compounds LL BM123, disclosed in U.S. Pat. No. 4,007,167. The compounds LL-BM123 are active against a variety of microorganisms and are useful in inhibiting the growth of such bacteria.

The compounds of the present invention are also active against a variety of microorganisms. However, they differ from LL BM123 in that the present compounds do not contain the spermidine substituent, 1,5,10-triazadecane. Further, the antibacterial effects of the new compounds on specific microorganisms, together with their chemical and physical properties, differentiate them from the previously described antibacterial agents.

DISCLOSURE OF THE INVENTION

Figure 1:
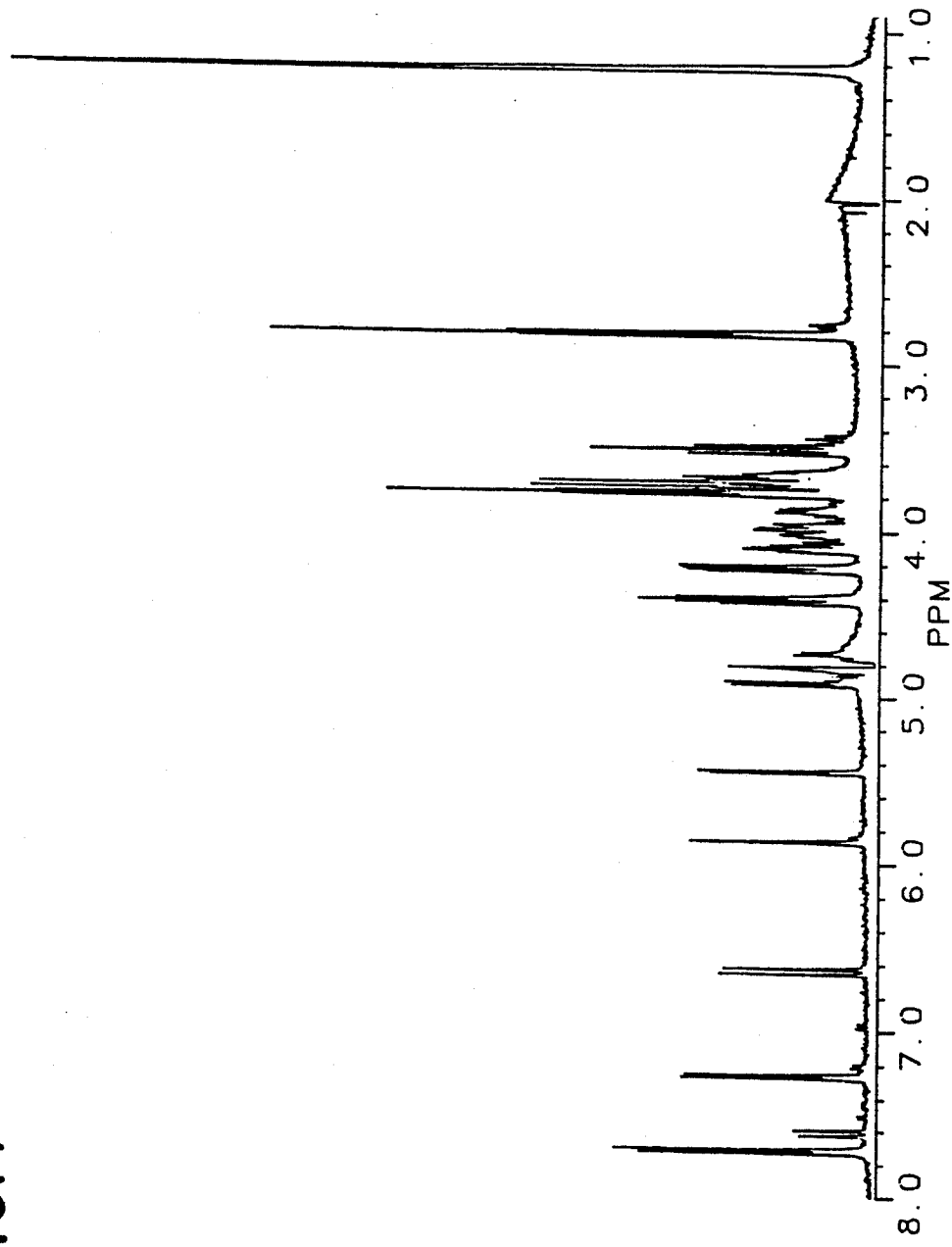
FIG. 1 is a hydrogen nuclear magnetic resonance spectrum of coumamidine gamma 1 at 500 MHz in $D_2O$.
Figure 2:
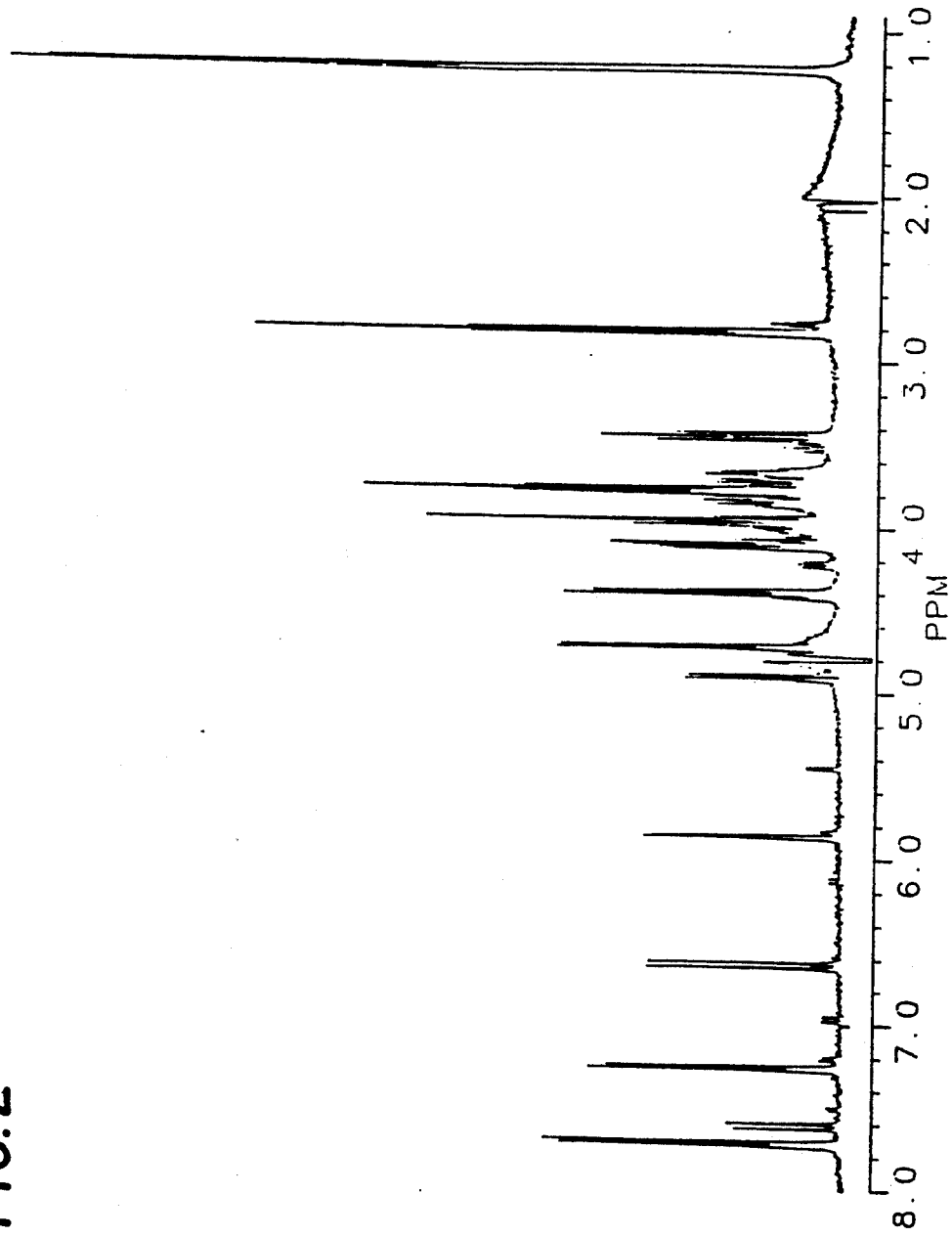
FIG. 2 is a hydrogen nuclear magnetic resonance spectrum of coumamidine gamma 2 at 500 MHz in $D_2O$.
Figure 3:
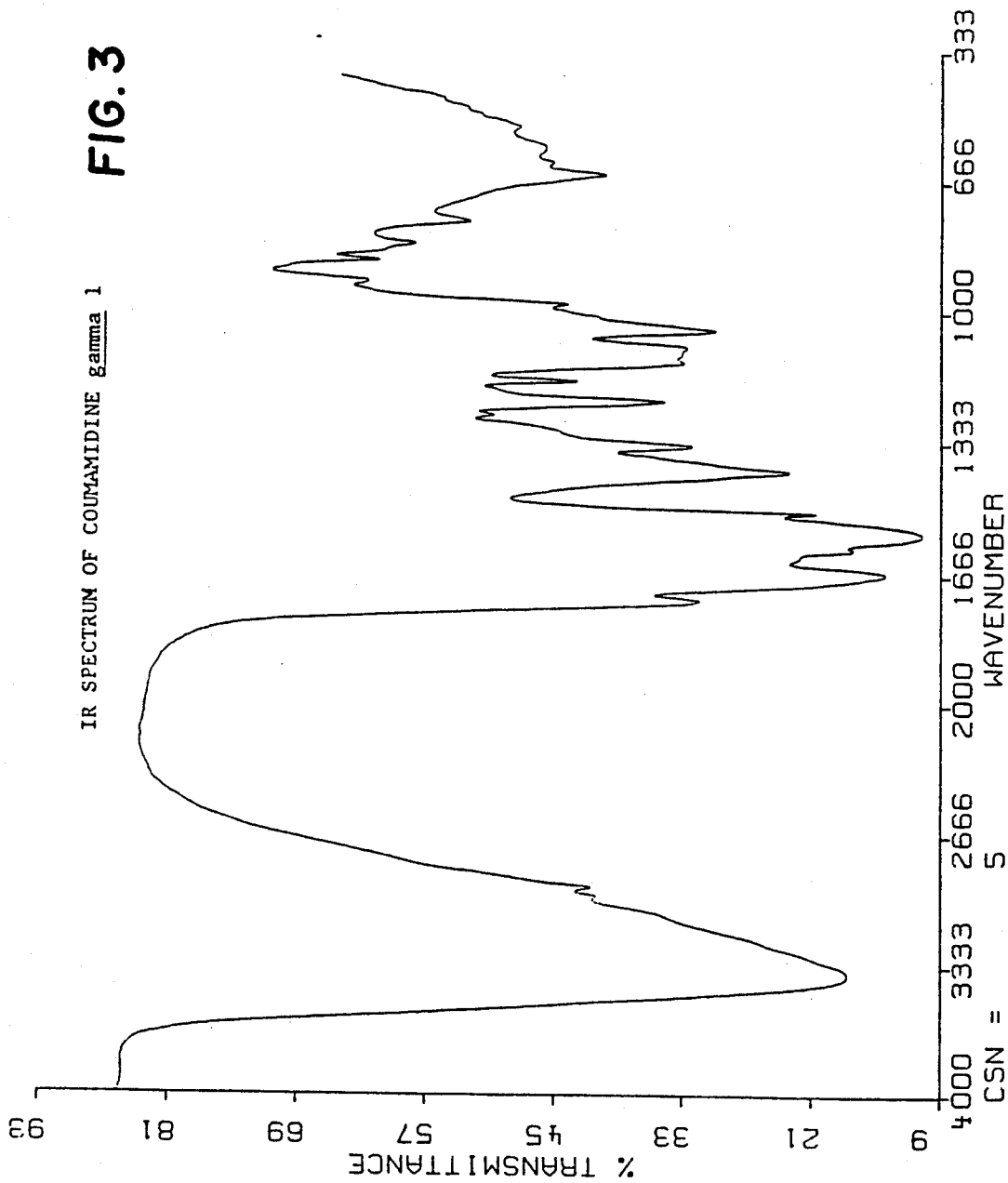
FIG. 3 is an infrared spectrum of coumamidine gamma 1 prepared in a KBr (potassium bromide) pellet.
Figure 4:
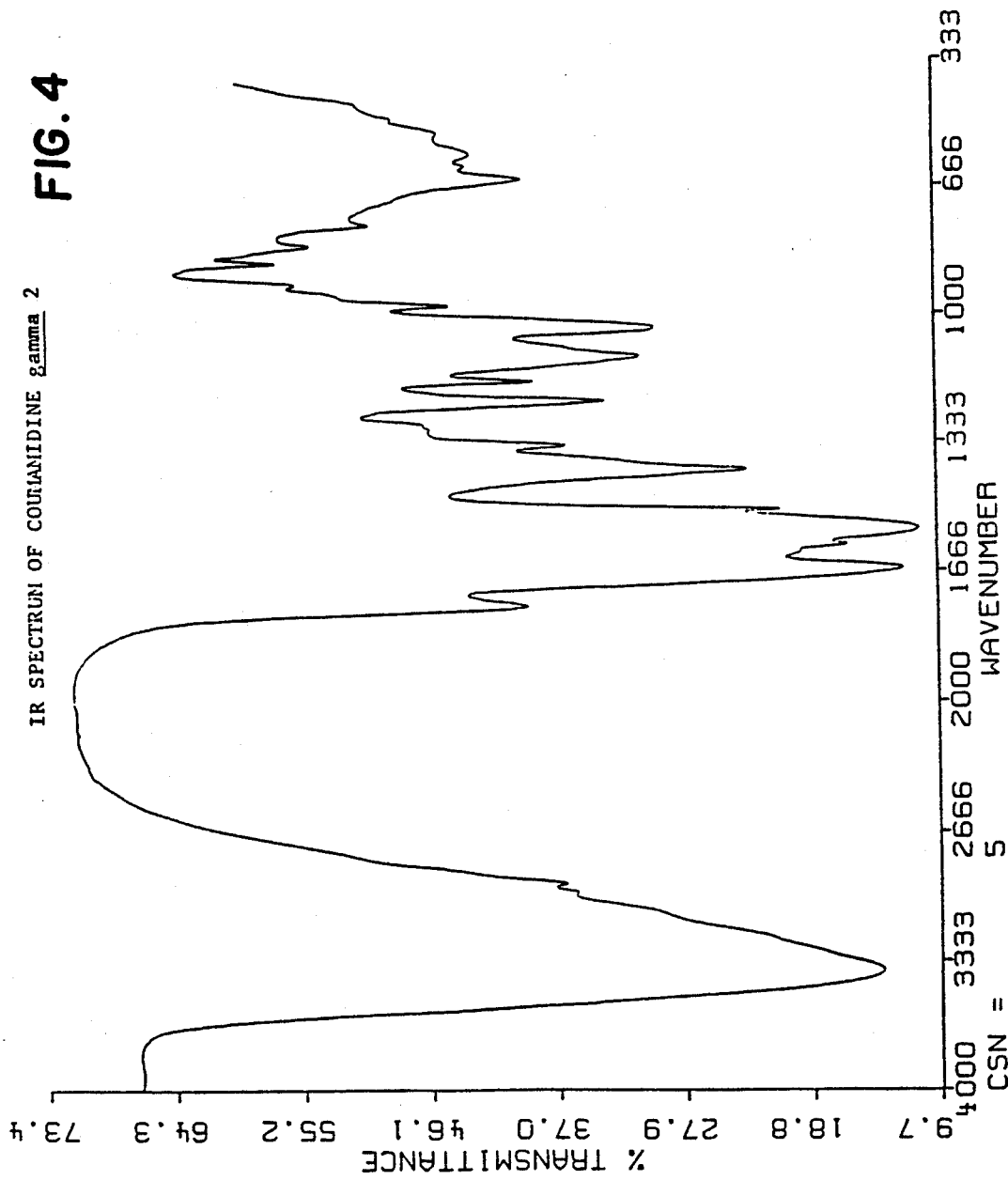
FIG. 4 is an infrared spectrum of coumamidine gamma 2 prepared in a KBr pellet.

The compounds and mixture of the compounds of the invention are made by cultivating the microorganism Saccharocolvsuora sp. AB 1167L 65. The microorganism produces branched mycelia. Spores are borne in chains on the aerial mycelium. The strain was isolated from soil collected at Russell, Ky. A subculture of this microorganism was deposited in the permanent collection of the Agricultural Research Service at Northern Regional Research Center, United States Department of Agriculture, 1815 North University Street, Peoria, Illinois 61604 U.S.A. The accession number for strain AB 1167L-65 is NRRL 18369.

Coumamidine gamma 1 and coumamidine gamma 2 are produced together by submerged aerobic fermentation (described in detail hereinbelow) of the microorganism Saccharopolyspora sp. strain AB 1167L-65. The compounds are recovered from fermentation broth filtrates of Saccharopolvsoora sp. strain AB 1167L 65 by solid phase extraction with an adsorption resin. Coumamidine gamma 1 and gamma 2 exhibit antibiotic activity against a broad spectrum of bacteria grown under aerobic conditions.

Morphology and Culture Characteristics

The meso isomer of diaminopimelic acid was found in whole-cell hydrolysates. Chromatography of the sugars in whole-cell hydrolysates showed arabinose and galactose as diagnostic sugars. Whole cell hydrolysates can be used to predict cell wall composition, and the combination of morphology and chemical composition can be used to classify aerobic actinomycetes into groups that are recognized based on their cell wall type. Lechevalier and Lechevalier, *Inter. J. Syst. Bacteriol.*, 20, 435–443, (1970), have developed such a classification scheme. The microorganism of this invention has a cell wall of Type IV, i.e., contains meso 2,6-diaminopimelic acid and has a type A whole-cell sugar pattern (arabinose and galactose).

The chemical composition of this microorganism was further characterized by analysis of the cellular lipids. Mycolic acids were not present. The major menaquinone was found to be tetrahydrogenated with nine isoprenoid units [MK $9(H_4)$]. Alderson, Goodfellow and Minnikin, J. Gen. Mirobiol., 131, 1671–1679 (1985). The polar lipids were found to contain phosphatidyl choline and phosphatidyl methylethanolamine giving a PIII phospholipid pattern. Lechevalier, De Bievre and Lechevalier, Biochem. System. Ecol., 5, 249–260 (1977). These findings are summarized in Table 1 below.

TABLE 1

| Lipid Analysis of Saccharopolyspora sp. AB 1167L-65 | |
| --- | --- |
| Mycolic acids | Not Present |
| Major menaquinone* | tetrahydrogenated with nine isoprenoid units |
| Polar lipids | phosphatidyl choline and phosphatidyl methylethanolamine |
| Phospholipid pattern** | PIII |

*MK-9($H_4$) Alderson, Goodfellow and Minnikin, J. Gen. Mirobiol., 131, 1671–1679 (1985)
**Containing the polar lipids phosphatidyl choline and phosphatidyl methylethanolamine. Lechevalier, De Bievre and Lechevalier, Biochem. System. Ecol., 5, 249–260 (1977)

The spore chains of Saccharopolyspora sp. AB 1167L 65 are straight to flexuous. The color of the aerial growth is white, yellowish white, or brownish pink. The surface of the aerial hyphae is ornamented with spiny protrusions.

The appearance and cultural characteristics of this microorganism in various media are described in greater detail in Table 2, The ability of Saccharopolyspora sp. AB 1167L-65 to grow on various carbon compounds in synthetic medium is shown in Table 3. Physiological characteristics are given in Table 4.

TABLE 2

| Cultural characteristics: Saccharopolyspora sp. AB 1167L-65 | |
| --- | --- |
| MEDIUM | CULTURAL CHARACTERISTICS* |
| Yeast extract-malt extract agar ISP 2 | G: Abundant<br>AM: White (263) and brownish pink (33)**<br>R: Light yellowish brown (76)<br>SP: Absent |
| Oatmeal agar ISP 3 | G: Moderate<br>AM: White (263)<br>R: Yellowish white (92)<br>SP: Absent |
| Inorganic salts-starch agar ISP 4 | G: Poor<br>AM: White (263)<br>SP: Absent |
| Glycerol-asparagine agar ISP 5 | G: Moderate<br>AM: White (263)<br>R: Pale yellow (89)<br>SP: Absent |
| Peptone-yeast extract-iron agar ISP 6 | G: Abundant<br>AM: Yellowish white (92)<br>R: Light yellowish brown (76)<br>SP: Absent |
| Tyrosine agar ISP 7 | G: Moderate<br>AM: White (263) and brownish pink (33)<br>R: Light yellowish brown (76)<br>SP: Absent |

TABLE 2-continued
Cultural characteristics: Saccharopolyspora sp. AB 1167L-65

| MEDIUM | CULTURAL CHARACTERISTICS* |
|---|---|
| Nutrient agar | G: Abundant |
| | AM: White (263) |
| | R: Light yellow (86) |
| | SP: Absent |
| Czapek's agar | G: Poor |
| | AM: Sparse; white (263) |
| | R: Yellowish white (92) |
| | SP: Absent |
| Calcium malate agar | G: Moderate |
| | AM: White (263) |
| | R: Grayish yellow (90) |
| | SP: Absent |
| | Calcium is partially solubilized |
| ATCC #172 | G: Moderate |
| | AM: White (263) |
| | R: Pale yellow (89) |
| | SP: Absent |
| Gause #1 modified (KNO$_3$ 0.1%, K$_2$HPO$_4$ MgSO$_4$ 0.05%, NaCl 0.05%, FeSO$_4$ 0.001%, starch 0.01%, yeast extract 0.01%, agar 1.5%) | G: Moderate |
| | AM: 0.05%, Pinkish white (9) |
| | R: Pinkish white (9) and white (263) |
| | SP: Absent |

Observations after incubation for 27 days at 28° C.
*Abbreviations: G = growth; AM = aerial mycelium; R = reverse; SP = soluble pigment
Color names and numbers in parentheses follow the color standard in Kelly, K. L. & D. B. Judd: ISCC-NBS Color-Name Charts Illustrated with Centroid Colors. U.S. Dept. of Comm. Suppl. to Cir. 553, Washington, D.C., 1976.

TABLE 3
Utilization of various compounds as the sole source of carbon* by Saccharopolyspora sp. AB 1167L-65.

| CARBON SOURCES | GROWTH |
|---|---|
| Adonitol | ++ |
| Arabinose | + |
| Cellulose | − |
| Dulcitol | − |
| Fructose | ++ |
| Galactose | + |
| Glucose | + |
| Inositol | − |
| Lactose | − |
| Maltose | + |
| Mannitol | ++ |
| Mannose | − |
| Melezitose | − |
| Melibiose | − |
| Raffinose | − |
| Rhamnose | + |
| Ribose | ++ |
| Salicin | − |
| Sorbitol | + |
| Starch | + |
| Sucrose | − |
| Trehalose | ++ |
| Xylose | − |

++ Good Utilization
+ Poor Utilization
− Did not utilize
Incubation at 28° C. for 43 days.
*Shirling, E. B. & D. Gottlieb: Methods for Characterization of Streptomyces species. Intern. J. Syst. Bacteriol., 16, 313-340 (1966).

TABLE 4
Physiological characteristics: Saccharopolyspora sp. AB 1167L-65.

| TEST | REACTION* |
|---|---|
| Starch hydrolysis | − |
| H$_2$S production | + |
| Melanin formation | |
| Peptone yeast extract-iron agar | − |
| Tyrosine agar | − |
| Litmus milk | Alkaline digestion |
| Decomposition of: | |
| Adenine | − |
| Casein | + |
| L-Tyrosine | + |
| NaCl tolerance | Growth at 7% but not 10% |
| Temperature range** | Growth at 21° C. to 37° C. No growth at or above 42° C. Optimum at 21° C. |

+ Reaction observed
− No reaction observed
*Observations after incubation for 27 days. Incubation at 28° C. except for the temperature range study.
**Medium ATCC #172

Fermentation

Although other culture methods are feasible, a liquid, submerged, agitated culture process is preferred. The culture is grown in a culture media which includes a source of carbon and a source of nitrogen. Media which are useful include an assimilable source of carbon such as starch, sugar, molasses, glycerol, a combination of glucose plus molasses, etc.; an assimilable source of nitrogen such as protein, protein hydrolysate, polypeptides, amino acids, peptone plus yeast extract or whole yeast, etc.; and other organic and inorganic ingredients which can be added to stimulate production of the antibiotic such as, for example, inorganic anions and cations including potassium, magnesium, calcium, ammonium, sulfate, carbonate, phosphate, chloride, etc. Further, buffers such as calcium carbonate can be added to aid in controlling the pH of the fermentation media.

Aeration can be provided by forcing sterile air through the fermenting medium. Agitation can be provided by shaking the container or by stirring the culture, for example, with a mechanical stirrer.

The fermentation is carried out in a temperature range of from about 24° C. to about 35° C. The pH of the fermentation is preferably maintained between from about pH 6 to about pH 9. The antibiotic is produced and accumulated from between 3 and 9 days after inoculation of the fermentation.

Isolation and Purification

The fermentation broth is filtered to remove the mycelial mass with Whatman ® filter paper (No 1). The filtrate is adjusted to pH 7 and mixed with Diaion HP-20 ® resin. The compounds displaying antibiotic activity (the determination of which is described in detail hereinbelow) are eluted from the resin with a step gradient from water to 100% methanol. This is the fermentation isolate of Saccharopolyspora sp. which shows antibacterial activity and which includes the compounds coumamidine gamma 1 and coumamidine gamma 2.

The product can be purified by drying the active fractions from the resin on a rotary evaporator and triturating the residue with acetone and methanol. The remaining water-soluble residue is chromatographed on a column of CM Sephadex ® resin available from Pharmacia. The product displaying antibiotic activity elutes from the column upon the application of a linear gradient of from 0% to 5% NaCl. Active fractions are desalted over a carbon column. The sample is thereafter chromatographed on a size exclusion column in a buffered solution.

Determination of Antibiotic Activity

The column effluent is monitored for antibiotic activity by an agar disc diffusion assay. A 20 microliter sample of each column fraction is applied to a paper disc. The discs are then placed on agar plates which were previously seeded with sufficient organism (*Pseudomonas aeruginosa* BMH1) to provide a turbid background, typically $10^5$ to $10^6$ colony forming units (CFU) per mL. The formation of a clear zone surrounding a paper disc is an indication that the fraction being tested contains a compound, or compounds with antibiotic activity.

The foregoing can be better understood by reference to the following examples which are provided for the illustration, and not the limitation, of the practice of the invention.

EXAMPLE 1

Saccharopolyspora sp. AB 1167L 65 (NRRL 18369) was maintained as frozen inoculum stock by freezing a portion of the original inoculum and storing at $-75°$ C. The medium N2B1 was used for both seed growth and for the fermentation. The ingredients for medium N2BI are shown in Table 5.

TABLE 5

| Medium N2B1 | |
| --- | --- |
| INGREDIENT | grams per liter |
| Glucose monohydrate | 20 |
| F-152 liquid peptone (made by Inolex Chemical Corporation, Chicago, IL) | 10 |
| Yeast extract (made by Difco Laboratories, Detroit, MI) | 1 |
| Molasses, Brer Rabbit ® green label (made by Del Monte Corporation, San Francisco, CA) | 5 |
| Calcium carbonate | 2 |

Distilled water to 1.0 liter.
The pH was not adjusted.

The medium was prepared for seeding as follows: Ten mL of the medium was dispensed into seed tubes. The tubes were $25 \times 150$ mm glass tubes which were covered with stainless steel caps. One hundred mLs of the medium was dispensed into 500 mL Erlenmeyer flasks. The flasks were plugged with rayon pharmaceutical coil. Thereafter, the tubes and flasks were sterilized for 35 minutes at 121° C., 15 psi.

Two seed steps were used. In the first step 0.5 mL of the frozen stored inoculum was inoculated into the $25 \times 150$ mm glass tubes each containing 10 mL of N2B1 medium. The tubes were incubated for 96 hours at 28° C. on a rotary shaker. In the second step, five percent vegetative inoculum from the tube growth was used to inoculate the seed flasks, each containing 100 mL of N2B1 medium. The seed flask was incubated for 72 hours at 28° C. on a rotary shaker operated at 250 rpm with a stroke of 5.7 cm.

Five percent vegetative inoculum from the second step seed flasks was then transferred aseptically to 200 500-mL Erlenmeyer flasks each containing 100 mL of medium N2B1. The fermentation flasks were incubated for 5 days at 28° C. on a rotary shaker operated at 250 rpm with a stroke of 5 7 cm. Afterwards, the fermentation flasks were harvested. The harvested volume was 19.5 liters.

EXAMPLE 2

The mycelial mass was removed from the fermentation broth from Example 1 by filtration through Whatman ® filter paper (No. 1). The filtrate was adjusted to pH 7 and stirred for 4 hours with 2 L of resin (Diaion HP-20 ®), and this mixture was allowed to stand for 12 hours at 4° C. The spent beer was decanted, and the resin was washed with 2 L of water. The compounds having antibiotic activity were eluted from the resin with two 2 L washings of 50% methanol/water and two 2 L washings of 50% acetonitrile and water. The washings were pooled, and the volume was reduced on a vertical evaporator. The sample was lyophilized to yield 35.3 g of crude material. The crude material was triturated with 200 mL of acetone and 200 mL of methanol. The insoluble material was redissolved in 100 mLs of water and adsorbed onto an ion exchange column (CM Sephadex ® resin), Na+ form ($2.5 \times 30$ cm), in distilled water. The column was washed with 500 mL of water, after which the compounds were eluted with a linear gradient of 0 to 5% NaCl over 4 liters of solvent. The fractions displaying antibiotic activity were pooled (350 mL) and adsorbed onto a bed of charred resin, such as Ambersorb ® resin (XE 347) manufactured by Rohm and Haas, ($2.5 \times 16$ cm). The column was washed with 300 mL of water, 300 mL of 50% methanol/water and 300 mL of 50% acetonitrile/water. The aqueous methanol and acetone fractions were combined and the solvent was removed to yield 110 mg of material with antibiotic activity. This material was dissolved in 2.5 mL of 50 mM ammonium acetate and chromatographed on a size exclusion column [Fractogel ® resin TSK (HW-40); $2.5$ cm $\times 100$ cm] and thereafter eluted with 50 mM ammonium acetate. The flow rate was 1.5 mL/min (22 psi), and 15 mL fractions were collected. The eluate was monitored at 254 nm. Material from two UV absorbant peaks, which correspond to fractions containing compounds with antibiotic activity, were collected at fractions numbered 120–125 and 126–155. The material that was collected corresponded to 61.6 mg of coumamidine gamma 1 and 9.1 mg of coumamidine gamma 2.

Characterization of the compounds coumamidine gamma 1 and coumamidine gamma 2.

The isomeric coumamidines, gamma 1 and gamma 2, are white powders, readily soluble in water and dimethylsulfoxide, slightly soluble in methanol. High resolution, positive ion fast atom bombardment (FAB) mass spectrometry established identical molecular ions of m/z 835.3576 for the two isomers corresponding to a formula of $C_{33}H_{49}N_{13}O_{13}$ (calc. 835.3577). UV lambda$_{max}$=286 nm. The coumamidine gamma 1 isomer has an imidazolidone ring at the 2 and 3 position of the terminal sugar, and the coumamidine gamma 2 isomer has an oxazolidone ring at positions 3 and 4 of the terminal sugar. Carbon-13 N.M.R. data are given in Table 6.

TABLE 6

| Tabulation of $^{13}C$ chemical shifts of Coumamidine gamma 1 and Coumamidine gamma 2 | | | |
| --- | --- | --- | --- |
| Coumamidine gamma 1 | | Coumamidine gamma 2 | |
| CARBON # | C Shift | CARBON # | C Shift |
| 6' | 17.1 | 6' | 17.1 |
| 2 | 33.2 | 2 | 33.2 |

TABLE 6 -continued

Tabulation of $^{13}C$ chemical shifts of Coumamidine gamma 1 and Coumamidine gamma 2

| Coumamidine gamma 1 | | Coumamidine gamma 2 | |
|---|---|---|---|
| CARBON # | C Shift | CARBON # | C Shift |
| 3 | 37.0 | 3 | 37.0 |
| 2″ | 55.4 | 2″ | 55.1 |
| 3‴ | 55.8 | 2‴ | 55.4 |
| 2′ | 56.8 | 2′ | 56.8 |
| 4′ | 57.9 | 4′ | 57.9 |
| 2‴ | 60.4 | 3‴ | 60.4 |
| 5″ | 64.2 | 5″ | 64.2 |
| 5‴ | 66.5 | 5‴ | 64.5 |
| 5′ | 68.8 | 5′ | 68.9 |
| 4‴ | 69.7 | 3′ | 70.5 |
| 3′ | 70.5 | 3″ | 73.1 |
| 3″ | 73.1 | 4‴ | 76.7 |
| 4″ | 74.8 | 4″ | 77.7 |
| 1″ | 82.1 | 1″ | 82.1 |
| 1′ | 95.7 | 1′ | 95.7 |
| 1‴ | 97.9 | 1‴ | 102.9 |
| 9 | 117.7 | 9 | 117.7 |
| 11 | 117.7 | 11 | 117.7 |
| 5 | 119.0 | 5 | 119.0 |
| 7 | 129.8 | 7 | 129.8 |
| 8 | 130.2 | 8 | 130.2 |
| 12 | 130.2 | 12 | 130.2 |
| 6 | 141.5 | 6 | 141.5 |
| 3‴, 2‴-urea | 156.5 | 10 | 157.5 |
| 10 | 157.5 | 2′-quanidino | 157.9 |
| 2′-quanidino | 158.0 | 4′-urea | 159.4 |
| 4′-urea | 159.5 | 2‴-urea | 160.8 |
| 2‴-urea | 160.9 | 2″-urea | 161.7 |
| 2″-urea | 161.8 | 3‴, 4‴carbamate | 162.8 |
| 1 | 169.5 | 1 | 169.5 |
| 4 | 169.6 | 4 | 169.6 |

Antimicrobial Activity

The antimicrobial activity of the coumamidine compounds of the present invention against a variety of aerobically grown bacteria is illustrated in Table 7. Minimum inhibitory concentration (MIC) was determined by the agar dilution method, described hereinbelow, using Brain Heart Infusion agar.

Twelve petri dishes were prepared, each containing successive aqueous 2-fold dilutions of the test compounds mixed with 10 mL of sterilized Brain Heart Infusion (BHI) agar. Each plate was inoculated with 1:100 (or 1:10 for slow growing strains (primarily Micrococcus and Streptococcus) dilutions of up to 32 different microrganisms, using a Steers replicator block calibrated to deliver approximately $10^4$ colony forming units (CFU). The inoculated plates are incubated at from about 35° C. to about 37° C. for approximately 20-24 hours. In addition, a control plate, using BHI agar containing no test compound, was prepared and incubated at the beginning, and the end, of each test. Ciprofloxacin was used as a control antibacterial.

After incubation, each petri dish was observed for the presence or absence of microorganism growth. The MIC was defined as the lowest concentration of test compound yielding no growth, a slight haze, or sparsely isolated colonies on the inoculum spot as compared to the growth control containing no test compound.

The results are indicated in the following table.

TABLE 7

Minimum inhibitory concentrations (microgram/mL) against bacteria grown aerobically.

| Organism | gamma 1 | gamma 2 | standard* |
|---|---|---|---|
| Staphylococcus aureus ATCC 6538P | 0.25 | 0.5 | 0.12 |
| Staphylococcus aureus CMX 686B | 0.25 | 0.5 | 0.12 |
| Staphylococcus aureus A5177 | 1.0 | 1.0 | 0.12 |
| Staphylococcus aureus 45 | 0.5 | 1.0 | 0.25 |
| Staphylococcus epidermidis 3519 | 0.5 | 1.0 | 0.5 |
| Enterococcus faecium ATCC 8043 | 16 | 32 | 1 |
| Streptococcus bovis A 5169 | 16 | 32 | 0.5 |
| Streptococcus agalactiae CMX 508 | 8 | 16 | 0.5 |
| Streptococcus pyogenes EES 614 | 4 | 1.0 | 0.5 |
| Streptococcus pyogenes 930 CONST | 2 | 1 | 0.25 |
| Escherichia coli JUHL | 0.25 | 0.5 | 0.008 |
| Escherichia coli SS | 0.5 | 1.0 | 0.004 |
| Enterobacter aerogenes ATCC 13048 | 1.0 | 2.0 | 0.015 |
| Enterobacter cloacae CMX 650A | 4 | 4 | 0.015 |
| Klebsiella pneumoniae ATCC 8045 | 0.25 | 0.5 | 0.015 |
| Serratia marcescens CMX 657E | 1.0 | 2.0 | 0.03 |
| Serratia marcescens CMX 740C | 2.0 | 2.0 | 0.03 |
| Proteus mirabilis CMX 704F | 1.0 | 1.0 | 0.015 |
| Proteus vulgaris ABBOTT JJ | 2.0 | 4 | 0.015 |
| Providencia stuartii CMX 640 | 0.5 | 2.0 | 0.025 |
| Pseudomonas aeruginosa A5007 | 8 | 16 | 0.12 |
| Pseudomonas aeruginosa ATCC 27853 | 8 | 8 | 0.25 |
| Pseudomonas aeruginosa BMH 10 | 0.25 | 0.5 | 0.06 |
| Pseudomonas aeruginosa CFS 387C | 8 | 16 | 0.12 |
| Pseudomonas aeruginosa CFS 389 | 8 | 8 | 0.12 |
| Pseudomonas aeruginosa K799/WT | 8 | 16 | 0.12 |
| Pseudomonas cepacia 2961 | 32 | >32 | 4 |
| Actinetobacter SP CMX 669 | 0.25 | 4 | 0.12 |
| Campylobacter jejuni ATTC 29428 | 0.06 | NT** | 0.25 |
| Haemophilus influenzae 503B | 0.03 | NT** | 0.002 |
| Neisseria gonorrhoeae 35FAMPI | 0.5 | NT** | 0.004 |
| Neisseria gonorrhoeae CMX 591 | 0.5 | NT** | 0.06 |

*Ciprofloxacin
**Not Tested against this strain.

Total daily dose administered to a host in single or divided doses may be in amounts, for example, from 0.001 to 100 mg/kg body weight daily and more usually 0.01 to 20 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed; the age, body weight, general health, sex and diet of the patient; the time of administration; the route of administration; the rate of excretion of the compound and its active metabolites; drugs used in combination, and the severity of the particular disease undergoing therapy.

The compounds of the present invention may be administered orally, nasally, opthalmically, parenterally, vaginally, rectally, topically or in an aerosol in dose unit formulations containing conventional nontoxic pharmaceutically acceptable carriers, adjuvants and vehicles, as desired. The term parenteral as used herein includes subcutaneous, intravenous, intramuscular or intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oil may be employed including synthetic mono- or diglycerides. In addition, fatty acids such as oleic acid find use in the preparation of injectables.

Suppositories for rectal or vaginal administration of the active compound may be prepared by mixing the active ingredient with a suitable, nonirritating excipient such as cocoa butter and polyethylene glycols which are solid at ordinary temperatures but liquid at the rectal/vaginal temperatures and will therefore melt in the rectum or vagina and release the active ingredient.

Solid dosage forms for the oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents and sweetening, flavoring, and perfuming agents.

The compounds of the invention can be used in treating infections caused by susceptible organisms in warm-blooded animals. They are useful for the treatment of infections of the urogenital, gastrointestinal, and respiratory systems, as well as infections of the ear, eye, skin, and soft tissues. They are useful for the treatment of opportunistic infections in burn patients.

The present invention includes within its scope the compounds in dilute forms, as crude concentrates, and in pure forms.

The compounds of the present invention are organic bases and are capable of forming acid-addition salts with a variety of organic and inorganic salt-forming reagents. Suitable acids include sulfuric, phosphoric, hydrochloric, hydrobromic, sulfamic, citric, oleic, fumaric, tartaric, acetic, benzoic, gluconic, ascorbic, and the like.

Further, the compounds of the present invention are capable of forming esters with, for example, acetate, propionate, butyrate, and the like.

The foregoing is merely illustrative of the invention and is not intended to limit the invention to the disclosed compounds. Variations and changes which are obvious to one skilled in the art are intended to be within the scope and nature of the invention as defined in the appended claims.

What is claimed is:

1. A fermentation isolate of Saccharopolyspora sp. AB 1167L-65 comprising compounds of the formulae:

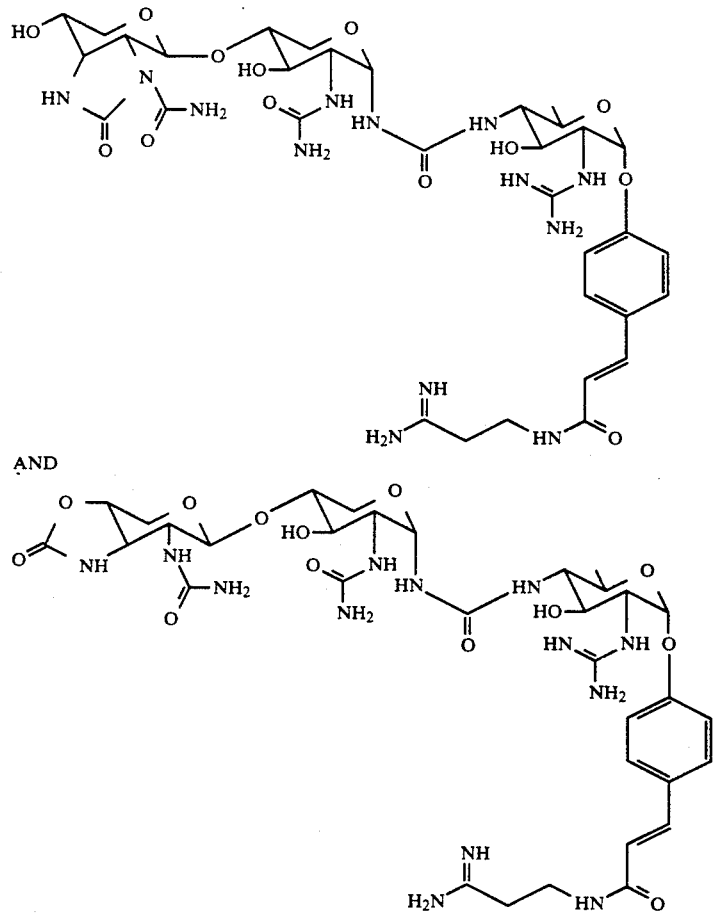

AND

2. A compound of the formula:

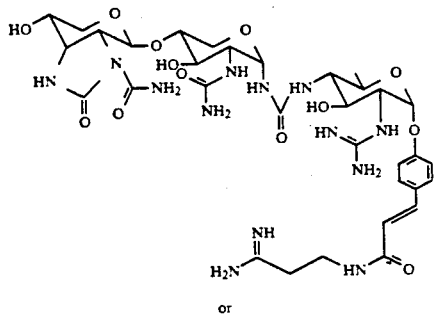

or

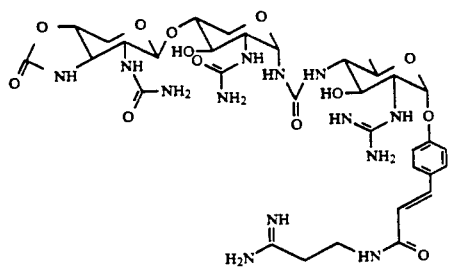

or a pharmaceutically acceptable acid-addition salt or ester thereof.

3. A process for producing the compounds coumamidine gamma 1 and coumamidine gamma 2 comprising culturing the microorganism Saccharopolyspora sp. AB 1167L-65 in a nutrient medium.

4. A pharmaceutical composition having antibacterial activity comprising a pharmaceutical carrier and a therapeutically effective amount of a compound of claim 2.

5. A method of treating a bacterial infection comprising administering to a patient in need thereof a therapeutically effective amount of a compound of claim 2.

UNITED STATES PATENT AND TRADEMARK OFFICE
CERTIFICATE OF CORRECTION

PATENT NO. : 5,171,740

DATED : December 15, 1992

INVENTOR(S) : J.B. McAlpine, R.J. Theriault, J.P. Karwowski, M. Jackson R.H. Chen It is certified that error appears in the above-identified patent and that said Letters Patent is hereby corrected as shown below:

Please add the Summary of Invention after column 1, line 25.

Summary Of The Invention

The compounds and the mixture of the invention comprise coumamidine gamma 1 (I) and coumamidine gamma 2 (II), which can be represented by the following structural formulas:

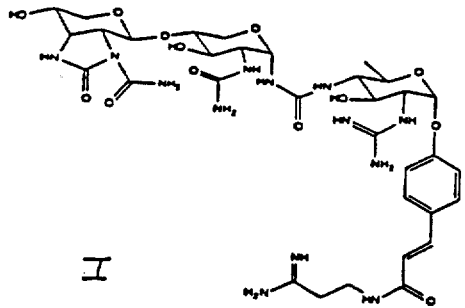

UNITED STATES PATENT AND TRADEMARK OFFICE
CERTIFICATE OF CORRECTION

PATENT NO. : 5,171,740

DATED : December 15, 1992

INVENTOR(S) : J.B. McAlpine, et al.

It is certified that error appears in the above-indentified patent and that said Letters Patent is hereby corrected as shown below:

Formula II continued:

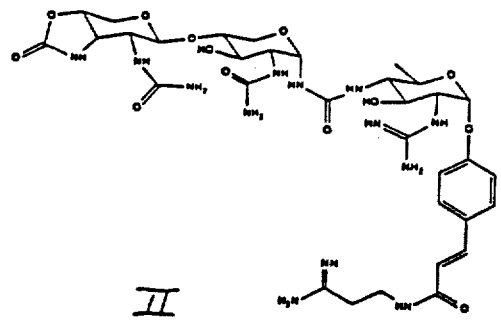

Signed and Sealed this

Twenty-sixth Day of April, 1994

Attest:

BRUCE LEHMAN

Attesting Officer

Commissioner of Patents and Trademarks